United States Patent [19]
Goodfellow et al.

[11] Patent Number: 5,871,545
[45] Date of Patent: Feb. 16, 1999

[54] PROSTHETIC KNEE JOINT DEVICE

[75] Inventors: John William Goodfellow, Summertown; John Joseph O'Connor, Qyarry Manor, both of England

[73] Assignee: BTG International Limited, London, England

[21] Appl. No.: 818,791

[22] Filed: Mar. 14, 1997

Related U.S. Application Data

[63] Continuation of PCT/GB95/02180, filed Sep. 14, 1995.

[30] Foreign Application Priority Data

Sep. 14, 1994 [GB] United Kingdom .................... 9418492

[51] Int. Cl.$^6$ ........................................................ A61F 2/38
[52] U.S. Cl. ................................................................ 623/20
[58] Field of Search ................................................ 623/20

[56] References Cited

U.S. PATENT DOCUMENTS

| | | | |
|---|---|---|---|
| 4,207,627 | 6/1980 | Cloutier | 623/20 |
| 4,216,549 | 8/1980 | Hillberry | 623/20 |
| 4,944,757 | 7/1990 | Martinez | 63/20 |
| 5,271,747 | 12/1993 | Wagner | 623/20 |
| 5,282,868 | 2/1994 | Bahler | 623/20 |
| 5,395,401 | 3/1995 | Bahler | 623/20 |
| 5,413,608 | 5/1995 | Keller | 623/20 |
| 5,609,639 | 3/1997 | Walker | 623/20 |
| 5,609,644 | 3/1997 | Ashby | 623/20 |

FOREIGN PATENT DOCUMENTS

| | | |
|---|---|---|
| 519 872 | 12/1992 | European Pat. Off. . |
| 546 726 | 6/1993 | European Pat. Off. . |
| 654 155 | 1/1995 | European Pat. Off. . |
| 2 663 536 | 12/1991 | France . |
| 1534263 | 11/1978 | United Kingdom . |
| 2245175 | 1/1992 | United Kingdom . |
| 2280376 | 2/1995 | United Kingdom . |

*Primary Examiner*—Michael J. Milano
*Attorney, Agent, or Firm*—Pillsbury Madison & Sutro LLP

[57] ABSTRACT

The invention concerns prosthetic knee joint devices, in particular of the meniscal type having femoral, tibial and meniscal components co-operable to allow congruence of the interfacing articulation surfaces while allowing close simulation of the natural joint in flexion-extension. The device features meniscal and tibial components each of one-piece bicompartmental construction having a pair of mutually spaced portions respectively defining condylar articulation surfaces, such portions being joined by way of an intercondylar portion, and the tibial and meniscal intercondylar portions being interengageable by means of complementary elements of a rib-and-groove joint arranged substantially in the antero-posterior direction, both the rib and the groove having curved side faces to allow limited long axis rotation between the components, and the groove being open at at least one end. With appropriate dimensioning, the device allows movement of the meniscal component in the antero-posterior direction, limited movement in the medio-lateral direction and limited long-axis rotation. It also provides in a simple and effective manner a securement against tibio-meniscal dislocation.

8 Claims, 1 Drawing Sheet

PROSTHETIC KNEE JOINT DEVICE

This is a Continuation of: International Appln. No. PCT/GB95/02180 filed Sep. 14, 1995 which designated the U.S.

BACKGROUND OF THE INVENTION

1. Field of the Invention

The invention concerns prosthetic knee joint devices.

2. Description of the Related Art

Various devices have been proposed in the past in attempting to provide a knee joint prosthesis which permits simulation of the natural joint function. Patent specification GB 1,534,263 describes a joint device referred to commonly and in this specification as a meniscal device which comprises femoral, tibial and meniscal components co-operable to allow congruence of the interfacing articulation surfaces while allowing close simulation of the natural joint in flexion-extension. Such devices can employ components of unicompartmental, bicompartmental or, in the case of the femoral component, tricompartmental form. The contents of patent specification GB 1,534,263 are included herein by reference.

In the case of the basic meniscal device, the joint components themselves offer no constraint against their mutual separation; freedom of movement being allowed under the control of the related soft tissues, which generally ensure that the meniscal component is retained in the desired manner between the associated components and cannot therefore dislocate. In some cases, however, it is appropriate to provide means to prevent or at least reduce the risk of dislocation of the meniscal component and some forms of the device have been developed to provide a mechanical coupling between the meniscal and tibial components with a view to ensuring the avoidance of dislocation. Patent specification GB 2,245,175 describes such a device, in which means are provided, separably connectable with the tibial component, to at least partially bridge the associated meniscal component to retain their interengagement. Other proposals have been put forward which feature some form of interengagement between a bicompartmental tibial component and a bicompartmental meniscal component, such as those described in EP-A-0 546 726 and EP-A-0 519 872.

SUMMARY OF THE INVENTION

The present invention has developed from the above thinking and arises out of the need to provide a device which will allow the required mobility and the required congruence with a clearly effective mechanical means for reducing risk of meniscal bearing dislocation. It is applicable to an assembly in which the meniscal and tibial components are each of one-piece bicompartmental construction having a pair of mutually spaced portions respectively defining individual condylar articulation surfaces, such portions being joined by way of an intercondylar portion.

According to the invention then, there is provided a prosthetic knee joint device of the type described above wherein the tibial and meniscal intercondylar portions are interengageable by means of complementary elements of a rib-and-groove joint arranged substantially in the antero-posterior direction, characterised in that both the rib and the groove have curved side faces to allow limited long axis rotation between the components, the rib having convexly curved side faces and the groove having concavely curved side faces, and in that the groove is open at at least one end.

To prevent axial dislocation of the tibio-meniscal interengagement, the rib-and-groove joint may be a dovetail joint with elements of appropriate dimensions.

In one embodiment, the elements of the rib-and-groove joint are dimensioned to provide a snap-fit interengagement when the two elements are engaged in an antero-posterior direction, in order to provide resistance to dislocation in an antero-posterior direction.

The widest section of the rib-and-groove joint may be offset from the centre in the antero-posterior direction, so providing that more resistance will be encoutered in dislocating the meniscal component in one direction than in engaging it in the opposite direction.

The device may include stop means to limit the relative movement between the meniscal and tibial components in the antero-posterior direction. To this end, a lip may be provided at the anterior side and/or at the posterior side of the tibial component, and the anterior lip, if provided, may be removably attachable to the tibial component.

BRIEF DESCRIPTION OF THE DRAWINGS

The device will now be described in more detail by way of example only with reference to the accompanying drawings in which.

DESCRIPTION OF THE PREFERRED EMBODIMENT

Figures 1, 2:
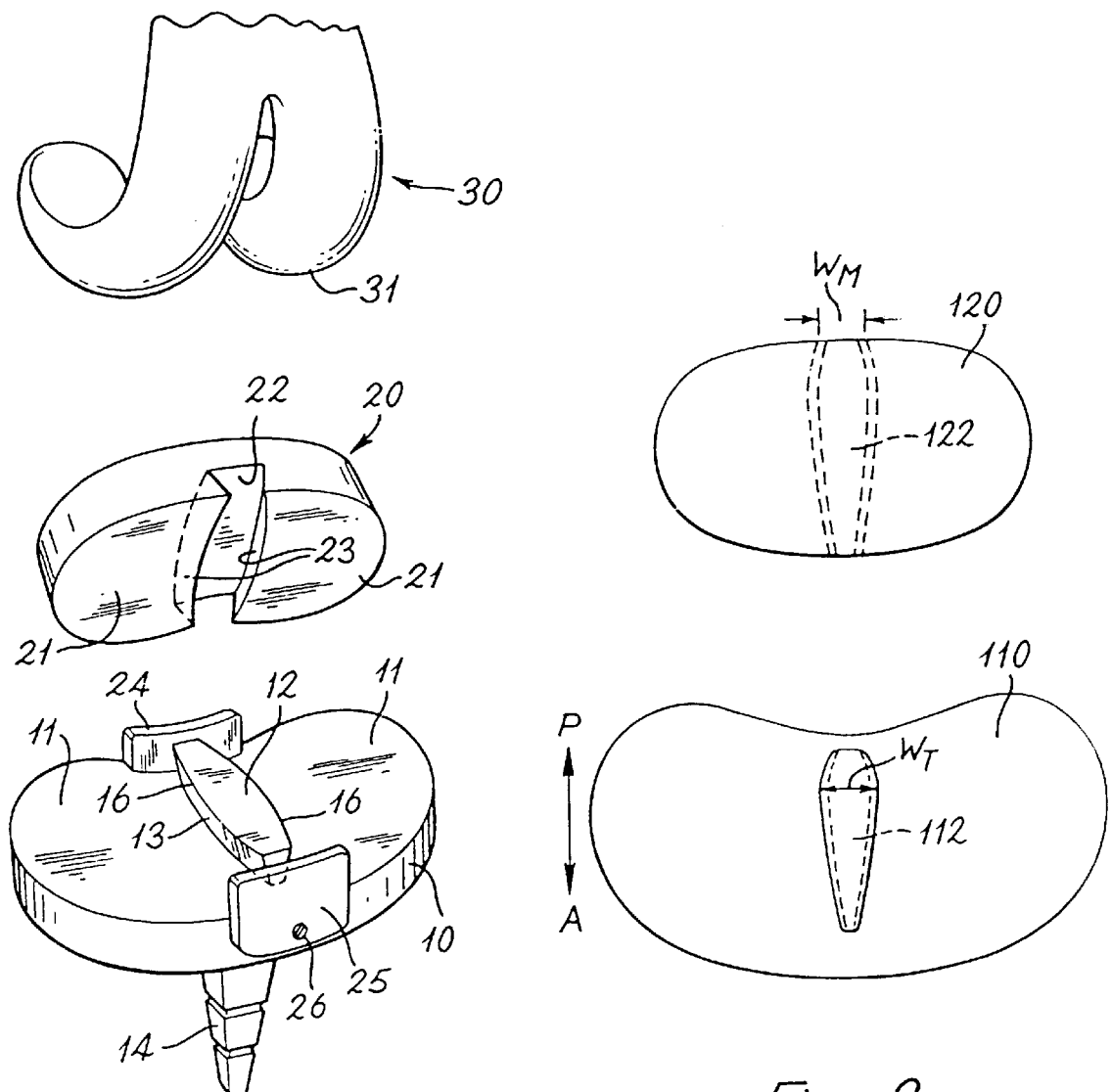
FIG. 1 schematically illustrates an exploded form of an embodiment of a device according to the invention.
FIG. 2 similarly represents an alternative embodiment of a device according to the invention.

In FIG. 1, the tibial, meniscal and femoral components are denoted by reference numbers 10, 20 and 30 respectively.

The tibial component 10 comprises a one-piece bicompartmental body for attachment to a suitably prepared surface of the proximal end of a patient's tibia, the downwardly projecting keel 14 serving to assist in attachment, which can be realised in a conventional manner by use of cement securement. The tibial component is provided with a pair of mutually spaced planar portions 11 defining individual condylar articulation surfaces, separated by an upstanding intercondylar flat-topped rib 12 of dovetail form, having convexly curved side faces 13 which mutually diverge in the upward direction and which are arranged to lie in an antero-posterior direction. The dovetail rib 12 therefore forms a guiding track which tapers from its widest section anteriorly and posteriorly.

The meniscal component 20 takes the form of a one-piece bicompartmental body of plate-like shape of smaller plan size than the tibial component. The inferior side of the meniscal component is provided with two mutually spaced planar portions 21 defining individual condylar articulation surfaces, the two portions 21 being separated by a shaped intercondylar dovetail groove 22. The dovetail groove has two mutually opposed concavely curved side walls 23 as shown, which are angled to converge in the downward direction, that is, towards the planar surfaces 21, at the same angle as the divergence of the side faces 13 of the rib 12. Between the faces 23, the dovetail rib 12 of the tibial component can be engaged, affording freedom of relative movement in the antero-posterior direction. The dovetail shaping of the elements of the rib-and-groove joint may if preferred be replaced by an alternative appropriate geometry. Particularly suitable are forms capable of resisting axial dislocation once the elements are engaged, and to this end a rib in the form of a Tee-sectioned rail and a complementary shaped groove are envisaged.

The edges 16 of the superior face of the rib 12 may, in one example, be designed as circular arcs. The groove 22 is shaped in a similar manner, tapering smoothly from a wider section groove centrally of the component to narrower sections at the front and back. Preferably, the curvature of the side faces of the groove is similar or identical, at least in part, to that of the side faces of the rib, such that when the mutually engaging surfaces come into abutment with one another, at least through medio-lateral movement, they may do so over a considerable contact surface area and so limit resulting contact stresses. The relative dimensions of the rib and groove are selected to provide a loose fit which serves to prevent axial dislocation but allows a degree of medio-lateral displacement and a degree of rotation about the long-axis of the joint.

The superior side (not shown) of the meniscal component provides a planar surface with two mutually spaced spherical recesses defining individual condylar articulation surfaces for articulation with the spherical condyles 31 of the femoral component 30. The femoral component is provided with means (not shown) to aid in securement to the prepared distal end of the patient's femur and is preferably of bicompartmental form as shown, or of tricompartmental form. It may alternatively be of twinned unicompartmental form.

In use of the assembly illustrated, the femoral and tibial components are secured in place to the ends of the femur and tibia respectively, and the femoral component is held away from the tibial platform. The meniscal component 20 is introduced from the front of the knee with the knee flexed, and the shaped groove 22 is engaged with the rib 12, planar portions 11 and 21 interfacing to provide the tibio-meniscal articulation. Thereafter the condylar surfaces of the femoral component 30 are located in the superior condylar recesses of the meniscal component before relocating the soft tissues of the joint and closing the knee capsule. The dimensions of the rib and of the groove are carefully selected so that the opening in the meniscal groove is able to pass the widest section of the rib of the tibial component when the meniscal component is engaged from the anterior side.

The precise dimensions of the rib and groove of the joint may be chosen as appropriate to the particular design requirements. The rib is preferably somewhat shorter than the groove in the antero-posterior direction, but clearly to limit the allowed long axis rotation, the length of the rib in the antero-posterior direction is greater than the width of the groove at the widest section.

It is to be noted that careful selection of the dimensions and geometry of the inter-engaging tibial and meniscal components is of great importance. The depth of the intercondylar groove 22 of the meniscal component is greater than the height by which the complementary rib 12 of the tibial component projects, to ensure that the weight is carried by the articulation surfaces 1 1, 21 and the dovetail parts of the connection are not involved in compressive load bearing between the components. The relative widths of the rib 12 and the groove 22 are such that, subsequent to interengagement, the two components cannot dislocate in an axial direction. However, the respective widths of the rib and of the groove are such that, with the planar surfaces 11 and 21 in engagement, the fit between the rib and the groove is a loose one allowing a degree of medio-lateral movement to allow some tolerance in the medio-lateral placement of the components. The relative geometries and dimensions of the rib 12 and of the groove 22 also permits a degree of rotation about the long-axis of the joint. Studies have shown that an axial rotation of the meniscal component on the tibial platform of ±15°–25° from alignment in the antero-posterior direction is desirable to accommodate the full range of joint movement in flexion/extension, this range being reduced if muscle activity around the joint is simulated. To avoid unnecessary mutual impingement of the faces 13 against the faces 23, and hence undesirable wear, the selected design of the rib and the groove may be such as to provide sufficient freedom of movement in axial rotation to ensure that the limitation is normally provided by the residual soft tissue, such as the collateral ligaments and the related muscles, and not by the geometry of the components. The loose fit between the rib and the groove and the shaping of the components also provides great flexibility in the location of the instantaneous centre of axial rotation of the meniscal component on the tibial platform, as it is known that in the natural joint during flexion/extension, the centre of long-axis rotation is not fixed, but moves around in the transverse plane.

It can be seen that the device as described permits the congruence of the horizontal articulation surfaces to be retained, whilst allowing movement in the antero-posterior direction, limited movement in the medio-lateral direction and limited long-axis rotation. It also provides in a simple and effective manner a securement against tibio-meniscal dislocation.

Although the device has so far been described as allowing unrestrained freedom of relative movement in the antero-posterior direction, it may be appropriate to provide some additional means to limit this movement. This is particularly the case in view of the lack of cruciate ligaments in a knee fitted with such an implant, which ligaments are largely responsible for providing stability in this direction in the undamaged knee. To this end the groove 22 may be closed at its anterior end and open at its posterior end only. Alternatively the invention envisages a fixed posterior lip at the posterior side of the tibial platform to provide a stop in the form of a wall limiting rearward travel of the meniscal component, as indicated in FIG. 1 by reference 24. Additionally or alternatively an attachable lip can be provided for securement to the anterior side of the tibial platform to be attached during surgery after the meniscal component has been introduced, to provide a stop limiting forward travel of the meniscal component. This element is indicated in FIG. 1 by reference 25, and is removably attached to the tibial component by means of screw 26. The meniscal component is smaller than the tibial platform in the antero-posterior dimension, such that it is still free to move through the normal range of movement in this direction without meeting the anterior and/or the posterior stop(s). Shaped lips 24 and 25 are preferred to pegs to serve the function of stops in order to distribute forces if the meniscal component does impact against either one of them.

FIG. 2 shows a further development of the concept of the invention, depicting the tibial and meniscal components in plan view. The width $W_M$ of the opening in the meniscal groove 122 is in this case slightly smaller than the width $W_T$ of the widest section of the tibial rib 112. When the meniscal component 120 is introduced to the tibial component 110 from the anterior side, it must therefore be engaged in a snap-fit manner. This gives a degree of resistance to antero-posterior dislocation, which may be employed as an alternative to or in addition to the stop or stops 24/25. As FIG. 2 shows, the widest section of the rib may be offset from its centre in the posterior direction, resulting in a shaping that tapers more sharply posteriorly than anteriorly. When the meniscal component is engaged from the anterior side, the narrowest section of the groove 122 passes relatively easily past the gently diverging side faces of the rib 1 12 and, with gentle concerted force, past the widest section of the rib. Subsequently, a considerably greater force will be required to anteriorly dislocate the meniscal component, as the rib presents much more sharply diverging side faces to the contacting faces of the groove.

In a manner conventionally recognised as being appropriate to devices of this sort, the tibial platform 10, 110 can be fabricated from a biocompatible metal, whilst the meniscal component 20, 120 is made from a low friction plastic material such as ultra high molecular weight polyethylene.

While the invention has been described with particular reference to the illustrated embodiments, it will be appreciated by the skilled reader that other variants are possible. For example, the dovetail joint elements could be inverted, by providing a downwardly projecting meniscal rib co-operating with a groove in the tibial platform.

We claim:

1. A prosthetic knee joint device of the meniscal type, including:

a femoral component for securing to a femur bone, a tibial component for securing to a tibia bone, and a meniscal component for engaging the tibial component, the meniscal component providing on one side articulation surfaces for articulation with the femoral component and the meniscal component providing on another side a pair of mutually spaced portions, such portions defining respective meniscal condylar articulation surfaces and such portions being joined by way of a meniscal intercondylar portion, the tibial component having a pair of mutually spaced portions, such portions defining respective tibial condylar articulation surfaces, and such portions being joined by way of a tibial intercondylar portion, the tibial and meniscal intercondylar portions including, for interengagement thereof, a rib-and-groove joint structure arranged substantially in an antero-posterior direction, the rib-and-groove joint structure including a rib having convexly curved side faces and a groove having concavely curved side faces, the groove being open at one end, the rib-and-groove joint structure providing a loose fit which serves to prevent axial dislocation but permits limited long axis rotation between the rib and groove.

2. A device according to claim 1, in which the rib-and-groove joint is a dovetail joint, the elements of the joint being dimensioned to prevent axial disengagement.

3. A device according to claim 1 or claim 2, wherein the groove is provided in the meniscal component.

4. A device according to claim 1, wherein the elements of the rib-and-groove joint structure are dimensioned to provide a snap-fit interengagement when the two elements are engaged in an antero-posterior direction.

5. A device according to claim 1, wherein the widest section of the rib-and-groove joint structure is offset from the centre in the antero-posterior direction.

6. A device according to claim 1, wherein stop means are provided to limit the relative movement between the meniscal and tibial components in the antero-posterior direction.

7. A device according to claim 6, wherein the stop means comprises a raised lip at the anterior side and/or at the posterior side of the tibial component.

8. A device according to claim 6, wherein the stop means comprises a raised lip at the anterior side of the tibial component and said anterior lip is removably attachable to the tibial component.

* * * * *